(12) United States Patent
Ferree

(10) Patent No.: US 9,433,404 B2
(45) Date of Patent: Sep. 6, 2016

(54) METHOD AND APPARATUS FOR CLOSING FISSURES IN THE ANNULUS FIBROSUS

(71) Applicant: Suture Concepts Inc., Basking Ridge, NJ (US)

(72) Inventor: Bret A. Ferree, Cincinnati, OH (US)

(73) Assignee: Suture Concepts Inc., Basking Ridge, NJ (US)

( * ) Notice: Subject to any disclaimer, the term of this patent is extended or adjusted under 35 U.S.C. 154(b) by 100 days.

(21) Appl. No.: 14/068,406

(22) Filed: Oct. 31, 2013

(65) Prior Publication Data

US 2014/0121682 A1 May 1, 2014

Related U.S. Application Data

(60) Provisional application No. 61/720,593, filed on Oct. 31, 2012.

(51) Int. Cl.
*A61B 17/00* (2006.01)
*A61B 17/04* (2006.01)
*A61B 17/06* (2006.01)

(52) U.S. Cl.
CPC ....... *A61B 17/0057* (2013.01); *A61B 17/0401* (2013.01); *A61B 2017/00663* (2013.01);
(Continued)

(58) Field of Classification Search
CPC .................. A61B 17/0466; A61B 2017/0446; A61B 2017/0448; A61B 2017/0461; A61B 2017/00663; A61B 17/0057; A61B 17/0401; A61B 2017/0404; A61B 2017/0409; A61B 2017/045; A61B 2017/0451; A61B 2017/0459; A61B 2017/0462; A61B 2017/0496; A61B 2017/06052; A61B 2017/0456; A61B 2017/0454; A61B 2017/06019; A61B 2017/0414; A61B 2017/0412; A61F 2002/30878; A61F 2002/0888; A61F 2002/0882; A61F 2002/0876; A61F 2002/087; A61F 2002/0864; A61F 2002/0858; A61F 2002/0852; A61F 2002/0847; A61F 2002/0841; A61F 2002/0835; A61F 2002/0829; A61F 2002/0823; A61F 2002/0817
USPC ....................................................... 606/232
See application file for complete search history.

(56) References Cited

U.S. PATENT DOCUMENTS 4,413,359 A 11/1983 Akiyama et al.
4,512,338 A 4/1985 Balko et al.
(Continued)

FOREIGN PATENT DOCUMENTS

DE 10340150 A1 3/2005
WO WO-03088876 A2 10/2003
(Continued)

*Primary Examiner* — Jonathan Miles
*Assistant Examiner* — George J Ulsh
(74) *Attorney, Agent, or Firm* — Pandiscio & Pandiscio

(57) ABSTRACT

A filament laterally spans a tear, fissure or other defect in an annulus. One portion of the filament is anchored to the annulus by passing at least one first anchor through the annulus and into the nucleus on one side of the fissure, and with a second portion of the filament being anchored to the annulus by passing at least one second anchor through the annulus and into the nucleus on a second side of the fissure, with the at least one first and second anchors being drawn back through the nucleus and against the inner surface of the posterior annulus by the application of a significant (e.g., about 15N to 25N) axial tension applied perpendicular to the posterior wall of the annulus, and with the fissure being drawn closed by the subsequent application of a significant axial tension applied perpendicular to the posterior wall of the annulus.

12 Claims, 3 Drawing Sheets

(52) U.S. Cl.
CPC .. *A61B2017/0404* (2013.01); *A61B 2017/045* (2013.01); *A61B 2017/0409* (2013.01); *A61B 2017/0451* (2013.01); *A61B 2017/0459* (2013.01); *A61B 2017/0462* (2013.01); *A61B 2017/0496* (2013.01); *A61B 2017/06052* (2013.01)

(56) References Cited

U.S. PATENT DOCUMENTS

| | | |
|---|---|---|
| 4,663,358 A | 5/1987 | Hyon et al. |
| 4,772,287 A | 9/1988 | Ray et al. |
| 4,834,757 A | 5/1989 | Brantigan |
| 4,904,260 A | 2/1990 | Ray et al. |
| 4,932,969 A | 6/1990 | Frey et al. |
| 5,015,255 A | 5/1991 | Kuslich |
| 5,047,055 A | 9/1991 | Bao et al. |
| 5,100,422 A | 3/1992 | Berguer et al. |
| 5,147,374 A | 9/1992 | Fernandez |
| 5,171,278 A | 12/1992 | Pisharodi |
| 5,192,326 A | 3/1993 | Bao et al. |
| 5,258,043 A | 11/1993 | Stone |
| 5,304,194 A | 4/1994 | Chee et al. |
| 5,342,394 A | 8/1994 | Matsuno et al. |
| 5,370,660 A | 12/1994 | Weinstein et al. |
| 5,390,683 A | 2/1995 | Pisharodi |
| 5,413,585 A * | 5/1995 | Pagedas ............ A61B 17/0469 606/151 |
| 5,425,772 A | 6/1995 | Brantigan |
| 5,540,715 A | 7/1996 | Katsaros et al. |
| 5,545,229 A | 8/1996 | Parsons et al. |
| 5,562,736 A | 10/1996 | Ray et al. |
| 5,645,597 A | 7/1997 | Krapiva |
| 5,681,310 A | 10/1997 | Yuan et al. |
| 5,716,416 A | 2/1998 | Lin |
| 5,735,877 A * | 4/1998 | Pagedas ............ A61B 17/0487 606/148 |
| 5,800,549 A | 9/1998 | Bao et al. |
| 5,800,550 A | 9/1998 | Sertich |
| 5,824,093 A | 10/1998 | Ray et al. |
| 5,827,328 A | 10/1998 | Buttermann |
| 5,879,366 A | 3/1999 | Shaw et al. |
| 5,916,225 A | 6/1999 | Kugel |
| 5,976,174 A | 11/1999 | Ruiz |
| 5,976,186 A | 11/1999 | Bao et al. |
| 6,015,428 A * | 1/2000 | Pagedas ............ A61B 17/0483 606/232 |
| 6,024,754 A | 2/2000 | Engelson |
| 6,245,107 B1 | 6/2001 | Ferree |
| 6,371,990 B1 | 4/2002 | Ferree |
| 6,402,750 B1 | 6/2002 | Atkinson et al. |
| 6,419,704 B1 | 7/2002 | Ferree |
| 6,425,919 B1 | 7/2002 | Lambrecht |
| 6,454,804 B1 | 9/2002 | Ferree |
| 6,482,235 B1 | 11/2002 | Lambrecht et al. |
| 6,491,724 B1 | 12/2002 | Ferree |
| 6,508,839 B1 | 1/2003 | Lambrecht et al. |
| 6,579,291 B1 | 6/2003 | Keith et al. |
| 6,592,625 B2 | 7/2003 | Cauthen |
| 6,645,247 B2 | 11/2003 | Ferree |
| 6,648,919 B2 | 11/2003 | Ferree |
| 6,648,920 B2 | 11/2003 | Ferree |
| 6,689,125 B1 | 2/2004 | Keith et al. |
| 6,719,797 B1 | 4/2004 | Ferree |
| 6,723,335 B1 | 4/2004 | Moehlenbruck et al. |
| 6,743,255 B2 | 6/2004 | Ferree |
| 6,755,863 B2 | 6/2004 | Ferree |
| 6,764,489 B2 | 7/2004 | Ferree |
| 6,805,695 B2 | 10/2004 | Keith et al. |
| 6,821,276 B2 | 11/2004 | Lambrecht et al. |
| 6,835,205 B2 | 12/2004 | Atkinson et al. |
| 6,843,790 B2 | 1/2005 | Ferree |
| 6,878,167 B2 | 4/2005 | Ferree |
| 6,883,520 B2 | 4/2005 | Lambrecht et al. |
| 6,936,072 B2 | 8/2005 | Lambrecht et al. |
| 6,969,404 B2 | 11/2005 | Ferree |
| 6,984,247 B2 | 1/2006 | Cauthen |
| 6,997,956 B2 | 2/2006 | Cauthen |
| 7,004,945 B2 | 2/2006 | Boyd et al. |
| 7,004,970 B2 | 2/2006 | Cauthen, III et al. |
| 7,033,393 B2 | 4/2006 | Gainor et al. |
| 7,033,395 B2 | 4/2006 | Cauthen |
| 7,048,764 B2 | 5/2006 | Ferree |
| 7,048,766 B2 | 5/2006 | Ferree |
| 7,052,516 B2 | 5/2006 | Cauthen, III et al. |
| 7,060,100 B2 | 6/2006 | Ferree et al. |
| 7,144,397 B2 | 12/2006 | Lambrecht et al. |
| 7,198,047 B2 | 4/2007 | Lambrecht et al. |
| 7,201,774 B2 | 4/2007 | Ferree |
| 7,201,775 B2 | 4/2007 | Gorensek et al. |
| 7,201,776 B2 | 4/2007 | Ferree et al. |
| 7,220,281 B2 | 5/2007 | Lambrecht et al. |
| 7,223,289 B2 | 5/2007 | Trieu et al. |
| 7,226,481 B2 | 6/2007 | Kuslich |
| 7,258,700 B2 | 8/2007 | Lambrecht et al. |
| 7,267,688 B2 | 9/2007 | Ferree |
| 7,273,497 B2 | 9/2007 | Ferree |
| 7,338,525 B2 | 3/2008 | Ferree |
| 7,341,590 B2 | 3/2008 | Ferree |
| 7,435,260 B2 | 10/2008 | Ferree |
| 7,445,634 B2 | 11/2008 | Trieu |
| 7,465,318 B2 | 12/2008 | Sennett et al. |
| 7,513,911 B2 | 4/2009 | Lambrecht et al. |
| 7,547,326 B2 | 6/2009 | Bhatnagar et al. |
| 7,553,330 B2 | 6/2009 | Lambrecht et al. |
| 7,556,649 B2 | 7/2009 | Moehlenbruck et al. |
| 7,556,650 B2 | 7/2009 | Collins et al. |
| 7,601,157 B2 | 10/2009 | Boyd et al. |
| 7,601,172 B2 | 10/2009 | Segal et al. |
| 7,608,108 B2 | 10/2009 | Bhatnagar et al. |
| 7,632,313 B2 | 12/2009 | Bhatnagar et al. |
| 7,670,380 B2 | 3/2010 | Cauthen, III |
| 7,682,393 B2 | 3/2010 | Trieu et al. |
| 7,682,400 B2 | 3/2010 | Zwirkoski |
| 7,717,961 B2 | 5/2010 | Lambrecht et al. |
| 7,740,659 B2 | 6/2010 | Zarda et al. |
| 7,740,660 B2 | 6/2010 | Collins et al. |
| 7,749,230 B2 | 7/2010 | Yuan et al. |
| 7,789,912 B2 | 9/2010 | Manzi et al. |
| 7,789,913 B2 | 9/2010 | Collins et al. |
| 7,799,833 B2 | 9/2010 | Boyd |
| 7,824,414 B2 | 11/2010 | Evans |
| 7,828,807 B2 | 11/2010 | LeHuec et al. |
| 7,837,733 B2 | 11/2010 | Collins et al. |
| 7,857,855 B2 | 12/2010 | Ferree |
| 7,857,857 B2 | 12/2010 | Kim |
| 7,867,278 B2 | 1/2011 | Lambrecht et al. |
| 7,879,102 B2 | 2/2011 | Slivka et al. |
| 7,879,103 B2 | 2/2011 | Gertzman et al. |
| 7,883,527 B2 | 2/2011 | Matsuura et al. |
| 7,901,430 B2 | 3/2011 | Matsuura et al. |
| 7,909,879 B2 | 3/2011 | Cauthen |
| 7,914,553 B2 | 3/2011 | Ferree |
| 7,935,147 B2 | 5/2011 | Wales |
| 7,947,080 B2 | 5/2011 | Ferree |
| 7,959,679 B2 | 6/2011 | Lambrecht et al. |
| 7,959,863 B2 | 6/2011 | Yamamoto et al. |
| 7,963,991 B2 | 6/2011 | Conner et al. |
| 7,993,343 B2 | 8/2011 | Lin et al. |
| 7,993,345 B2 | 8/2011 | Yuan et al. |
| 7,998,208 B2 | 8/2011 | Kohm et al. |
| 7,998,213 B2 | 8/2011 | Lambrecht et al. |
| 8,007,500 B2 | 8/2011 | Lin et al. |
| 8,012,211 B2 | 9/2011 | Kuslich |
| 8,021,425 B2 | 9/2011 | Lambrecht |
| 8,025,698 B2 | 9/2011 | Lambrecht |
| 8,048,618 B2 | 11/2011 | Luk et al. |
| 8,062,337 B2 | 11/2011 | Bruneau et al. |
| 8,070,818 B2 | 12/2011 | Bhatnagar et al. |
| 8,075,618 B2 | 12/2011 | Trieu et al. |
| 8,075,619 B2 | 12/2011 | Ferree |
| 8,092,536 B2 | 1/2012 | Ahrens et al. |
| 8,100,973 B2 | 1/2012 | Sennett et al. |
| 8,105,382 B2 | 1/2012 | Olmos et al. |
| 8,109,978 B2 | 2/2012 | Ferree |

(56) References Cited

U.S. PATENT DOCUMENTS

| | | |
|---|---|---|
| 8,114,161 B2 | 2/2012 | Evans et al. |
| 8,162,993 B2 | 4/2012 | Ferree |
| 8,163,019 B2 | 4/2012 | Bao et al. |
| 8,177,810 B2 | 5/2012 | Ferree |
| 8,177,847 B2 | 5/2012 | Bhatnagar et al. |
| 8,197,544 B1 | 6/2012 | Manzi et al. |
| 8,211,126 B2 | 7/2012 | Yeh et al. |
| 8,224,465 B2 | 7/2012 | Tantawi et al. |
| 8,231,678 B2 | 7/2012 | Lambrecht |
| 8,246,630 B2 | 8/2012 | Manzi et al. |
| 8,252,031 B2 | 8/2012 | Carls et al. |
| 8,257,437 B2 | 9/2012 | Lambrecht et al. |
| 8,267,939 B2 | 9/2012 | Cipoletti et al. |
| 8,267,943 B2 | 9/2012 | Ferree |
| 8,317,802 B1 | 11/2012 | Manzi et al. |
| 8,317,868 B2 | 11/2012 | Bhatnagar et al. |
| 8,337,528 B2 | 12/2012 | Ferree |
| 8,337,529 B2 | 12/2012 | Ferree |
| 8,337,557 B2 | 12/2012 | Collins et al. |
| 8,449,614 B2 | 5/2013 | Ferree |
| 8,450,288 B2 | 5/2013 | Boyd |
| 8,470,043 B2 | 6/2013 | Schaller et al. |
| 8,506,633 B2 | 8/2013 | Trieu |
| 8,535,338 B2 | 9/2013 | Wales et al. |
| 8,568,481 B2 | 10/2013 | Olmos et al. |
| 8,603,118 B2 | 12/2013 | Yeh et al. |
| 8,603,170 B2 | 12/2013 | Cipoletti et al. |
| 8,679,179 B2 | 3/2014 | Ferree |
| 8,679,180 B2 | 3/2014 | Ferree |
| 2002/0032155 A1 | 3/2002 | Ferree |
| 2002/0128713 A1 | 9/2002 | Ferree |
| 2002/0151896 A1 | 10/2002 | Ferree |
| 2002/0151981 A1 | 10/2002 | Ferree |
| 2002/0156532 A1 | 10/2002 | Ferree |
| 2002/0156533 A1 | 10/2002 | Ferree |
| 2002/0161367 A1 | 10/2002 | Ferree |
| 2002/0165542 A1 | 11/2002 | Ferree |
| 2003/0004574 A1 | 1/2003 | Ferree |
| 2003/0040796 A1 | 2/2003 | Ferree |
| 2003/0074076 A1 | 4/2003 | Ferree et al. |
| 2003/0078579 A1 | 4/2003 | Ferree |
| 2003/0185812 A1 | 10/2003 | Ferree |
| 2003/0191536 A1 | 10/2003 | Ferree |
| 2003/0195631 A1 | 10/2003 | Ferree |
| 2003/0204260 A1 | 10/2003 | Ferree |
| 2004/0010318 A1 | 1/2004 | Ferree |
| 2004/0092945 A1 | 5/2004 | Ferree |
| 2004/0093087 A1 | 5/2004 | Ferree et al. |
| 2004/0093092 A1 | 5/2004 | Ferree |
| 2004/0097980 A1 | 5/2004 | Ferree |
| 2004/0138753 A1 | 7/2004 | Ferree |
| 2004/0143334 A1 | 7/2004 | Ferree |
| 2004/0148028 A1 | 7/2004 | Ferree et al. |
| 2004/0186573 A1 | 9/2004 | Ferree |
| 2004/0186577 A1 | 9/2004 | Ferree |
| 2004/0220101 A1 | 11/2004 | Ferree |
| 2004/0220102 A1 | 11/2004 | Ferree |
| 2004/0225290 A1 | 11/2004 | Ferree |
| 2004/0230310 A1 | 11/2004 | Ferree |
| 2004/0236342 A1 | 11/2004 | Ferree et al. |
| 2004/0244806 A1 | 12/2004 | Ferree |
| 2004/0249459 A1 | 12/2004 | Ferree |
| 2004/0249461 A1 | 12/2004 | Ferree |
| 2004/0249465 A1 | 12/2004 | Ferree |
| 2004/0260396 A1 | 12/2004 | Ferree et al. |
| 2005/0033338 A1 | 2/2005 | Ferree |
| 2005/0065089 A1 | 3/2005 | Ferree |
| 2005/0165484 A1 | 7/2005 | Ferree |
| 2005/0256582 A1 | 11/2005 | Ferree |
| 2005/0261773 A1 | 11/2005 | Ferree |
| 2006/0004454 A1 | 1/2006 | Ferree et al. |
| 2006/0052870 A1 | 3/2006 | Ferree |
| 2006/0064169 A1 | 3/2006 | Ferree |
| 2006/0212121 A1 | 9/2006 | Ferree |
| 2006/0217747 A1 | 9/2006 | Ferree |
| 2006/0235535 A1 | 10/2006 | Ferree et al. |
| 2006/0247665 A1 | 11/2006 | Ferree |
| 2006/0247778 A1 | 11/2006 | Ferree et al. |
| 2007/0027471 A1 | 2/2007 | Ferree |
| 2007/0038231 A1 | 2/2007 | Ferree |
| 2007/0055375 A1 | 3/2007 | Ferree |
| 2007/0067040 A1 | 3/2007 | Ferree |
| 2007/0135920 A1 | 6/2007 | Ferree |
| 2007/0142839 A1 | 6/2007 | Ferree |
| 2007/0156152 A1 | 7/2007 | Ferree |
| 2007/0168043 A1 | 7/2007 | Ferree |
| 2007/0276494 A1 | 11/2007 | Ferree |
| 2007/0288040 A1 | 12/2007 | Ferree |
| 2008/0014179 A1 | 1/2008 | Ferree |
| 2008/0027459 A1 | 1/2008 | Ferree |
| 2008/0125779 A1 | 5/2008 | Ferree |
| 2008/0125780 A1 | 5/2008 | Ferree |
| 2008/0140123 A1 | 6/2008 | Ferree |
| 2008/0140126 A1 | 6/2008 | Ferree |
| 2008/0195119 A1 | 8/2008 | Ferree |
| 2008/0195151 A1 | 8/2008 | Ferree |
| 2008/0221686 A1 | 9/2008 | Ferree |
| 2008/0228230 A1 | 9/2008 | Ferree |
| 2008/0243256 A1 | 10/2008 | Ferree |
| 2008/0311114 A1 | 12/2008 | Ferree |
| 2009/0024165 A1 | 1/2009 | Ferree |
| 2010/0016889 A1 | 1/2010 | Ferree |
| 2010/0069957 A1* | 3/2010 | Abuzaina et al. ............ 606/228 |
| 2010/0174328 A1 | 7/2010 | Seaton, Jr. et al. |
| 2010/0318091 A1 | 12/2010 | Linares |
| 2011/0034975 A1 | 2/2011 | Ferree |
| 2011/0178602 A1 | 7/2011 | Ferree |
| 2011/0190893 A1 | 8/2011 | Ferree |
| 2011/0218573 A1 | 9/2011 | Ferree |
| 2011/0264224 A1 | 10/2011 | Ferree |
| 2011/0288647 A1 | 11/2011 | Ferree |
| 2011/0295276 A1 | 12/2011 | Wales et al. |
| 2012/0071896 A1 | 3/2012 | Ferree |
| 2012/0089162 A1 | 4/2012 | Ferree |
| 2012/0116514 A1 | 5/2012 | Kuslich et al. |
| 2012/0277766 A1 | 11/2012 | Ferree |
| 2013/0013005 A1 | 1/2013 | Ferree |
| 2013/0131728 A1 | 5/2013 | Ferree |
| 2013/0226271 A1 | 8/2013 | Ferree |
| 2013/0274809 A1 | 10/2013 | Ferree |
| 2014/0005786 A1 | 1/2014 | Lambrecht |

FOREIGN PATENT DOCUMENTS

| | | |
|---|---|---|
| WO | WO-2006028986 A2 | 3/2006 |
| WO | WO-2011057394 A1 | 5/2011 |

* cited by examiner

METHOD AND APPARATUS FOR CLOSING FISSURES IN THE ANNULUS FIBROSUS

REFERENCE TO RELATED APPLICATION

This application claims priority from U.S. Provisional Patent Application Ser. No. 61/720,593, filed Oct. 31, 2012, the entire content of which is incorporated herein by reference.

FIELD OF THE INVENTION

This invention relates to the treatment of intervertebral disc herniation and degenerative disc disease in general and, more particularly, to methods and apparatus for closing fissures in the annulus fibrosus.

BACKGROUND OF THE INVENTION

The human intervertebral disc is an oval to kidney bean-shaped structure of variable size depending on its location in the spine. The outer portion of the disc is comprised of a tissue known as the annulus fibrosus (or anulus fibrosus, annulus fibrosis, anulus fibrosis, or simply "the annulus"). The inner portion of the disc is comprised of a tissue known as the nucleus pulposus, or simply "the nucleus".

The annulus is made up of ten to twenty collagen fiber lamellae. The collagen fibers within a given lamella are parallel to one another. Successive lamellae are oriented in alternating directions. About 48 percent of the lamellae are incomplete, but this value varies with location and it increases with age. On average, the lamellae lie at an angle of about 60 degrees to the vertebral axis line, but this too varies with location. The orientations of the lamellae serve to control vertebral motion (i.e., one half of the bands tighten to check motion when the vertebra above or below the disc are turned in either direction).

The annulus contains the nucleus, which has a consistency generally similar to that of crabmeat. The nucleus serves to transmit and dampen axial loads. A high water content (approximately 70-80 percent) assists the nucleus in this function. The water content has a diurnal variation. The nucleus imbibes water while a person lies recumbent. Nuclear material removed from the body and placed into water will imbibe water, swelling to several times its normal size. Activity generates increased axial loads, which squeeze fluid from the disc. The nucleus comprises roughly 50 percent of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes, or "degenerates", with age. As a person ages, the water content of the disc falls from approximately 85 percent at birth to approximately 70 percent in the elderly. The ratio of chondroitin sulfate to keratin sulfate decreases with age, while the ratio of chondroitin 6 sulfate to chondroitin 4 sulfate increases with age. The distinction between the annulus and the nucleus decreases with age. Generally, disc degeneration is painless.

Premature or accelerated disc degeneration is known as degenerative disc disease. A large portion of patients suffering from chronic lower back pain are thought to have this condition. As the disc degenerates, the nucleus and annulus functions are compromised. The nucleus becomes thinner and less able to handle compressive loads. The annulus fibers become redundant as the nucleus shrinks. The redundant annular fibers are less effective in controlling vertebral motion. This disc pathology can result in: (1) bulging of the annulus into the spinal cord or nerves; (2) narrowing of the space between the vertebrae where the nerves exit; (3) tears of the annulus (both "full-thickness" and "partial-thickness" tears) as abnormal loads are transmitted to the annulus and the annulus is subjected to excessive motion between vertebrae; and (4) disc herniation or extrusion of the nucleus through complete (i.e., full-thickness) annular tears. Degenerative disc disease is frequently the cause of substantial pain for a patient.

Current surgical treatments for disc degeneration are generally "destructive", in the sense that they involve the removal or destruction of disc tissue. One group of procedures, which includes lumbar discectomy, removes the nucleus or a portion of the nucleus. A second group of procedures destroys nuclear material. This group includes chymopapin (an enzyme) injection, laser discectomy, and thermal therapy (i.e., heat treatment to denature proteins in the nucleus). The first two groups of procedures compromise the nucleus of the treated disc. A third group of procedures, which includes spinal fusion procedures, either removes the disc or eliminates the disc's function by connecting together two or more vertebrae, e.g., by "fusing" the vertebrae together with bone. However, such spinal fusion procedures transmit additional stress to the adjacent discs, which typically results in premature degeneration of the adjacent discs. In general, the "destructive" nature of current surgical treatments for disc degeneration can provide substantial pain relief for the patient, but it can also lead to the acceleration of adjacent disc degeneration, which can result in new pain for the patient.

Prosthetic disc replacement offers many advantages. The prosthetic disc attempts to eliminate a patient's pain while preserving the disc's function. Current prosthetic disc implants either replace the nucleus or replace both the nucleus and the annulus. Both types of implants require the removal of the degenerated disc component to allow room for the replacement prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements may cause lower back pain if too much pressure is applied to the annulus. As discussed in U.S. Pat. Nos. 6,878,167 and 7,201,774, the content of each being expressly incorporated herein by reference in their entirety, the posterior portion of the annulus has abundant pain fibers.

Herniated nucleus pulposus occurs from tears (or "fissures") in the annulus. The herniated nucleus material often applies pressure to the nerves or spinal cord. Compressed nerves can cause back and leg or arm pain. Although a patient's symptoms result primarily from the pressure caused by the herniated nucleus, the primary pathology lies in the torn annulus.

Surgery for the herniated nucleus, which is sometimes referred to as a microlumbar discectomy, only addresses the herniated nucleus. With such surgery, the surgeon removes the herniated nucleus material, which is pressing on the nerves or spinal cord. In addition, in order to reduce the risk of extruding additional pieces of nucleus through the defect in the annulus, the surgeon also generally remove generous amounts of the nucleus still within the annulus. However, this generally requires that the tear or fissure in the annulus be enlarged so as to allow the surgeon access to the nucleus material still within the annulus, and this enlargement of the tear or fissure further weakens the annulus. As a result, while a microlumbar discectomy frequently decreases or eliminates a patient's back and leg or arm pain, the procedure typically further damages the already-weakened discs, which may lead to the creation of future pain for the patient.

Thus there is a need for a new and improved method and apparatus for closing fissures in the annulus.

SUMMARY OF THE INVENTION

This invention relates to the treatment of intervertebral disc herniation and degenerative disc disease in general and, more particularly, to methods and apparatus for closing fissures in the annulus fibrosus (AF) or, simply the annulus (A). In one preferred form of the present invention, a first anchor component is inserted through the annulus and into the nucleus. Tension on the flexible longitudinal fixation component (e.g., the filament), in an axial direction, of for example of 15N to 25N, pulls the anchor through the nucleus tissue and against the inner layer of the annulus. A second anchor component is then inserted through the annulus, generally on the opposite side of a defect or fissure in the annulus and into the nucleus. Tension on the flexible longitudinal fixation component, in an axial direction, of for example of 15N to 25N, pulls the anchor through the nucleus tissue and against the inner layer of the annulus. Such tension also pulls the flexible longitudinal fixation component through the opening or openings in the second anchor, which increases the tension on the portion of the flexible longitudinal fixation component that extends between the anchors (lateral tension), which preferably pulls the annulus tissue on either side of the fissure together.

Additional tension on the flexible longitudinal fixation component then pulls a portion or portions of that flexible component into narrow slit-like openings in the anchor, which fastens those components together. Additional anchor components, for example, three, four, five, or more anchors, which have flexible longitudinal fixation component locking or fastening features can be preferably placed in the disc using the same method. A single flexible longitudinal fixation component preferably connects such anchors. This approach eliminates post-operative anchor migration through the nucleus, and thereby reduces the tension across a fissure, and hence can allow nucleus material to migrate into and through the fissure. Anchor components firmly seated against the inner layer of the annulus, preferably in a sequential manner during surgery are not subject to such post-operative migration and therefore maintain the desired tension across the fissure, which prevents the migration of even small amounts of nucleus material into or across the fissure.

The present invention may also be used to close other soft tissue defects in the bodies of humans or animals. And the flexible longitudinal fixation components (e.g., the filaments) may be anchored to one of the upper and lower vertebral bodies.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE INVENTION

Figure 1:
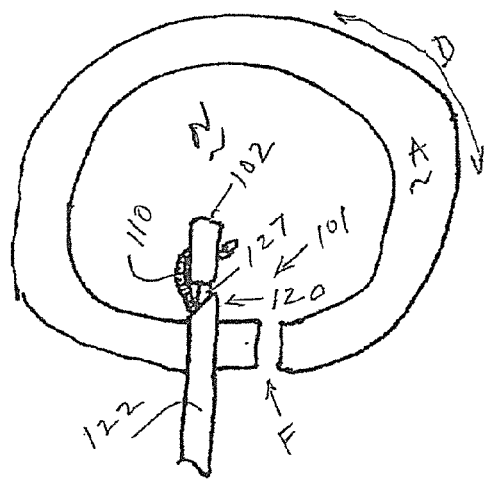
FIG. 1 is a schematic view showing one preferred form of apparatus for closing a fissure in the annulus penetrating the annulus on one side of a fissure.

The present invention provides a new and improved method and apparatus for closing fissures in the annulus. More particularly, the present invention facilitates the reconstruction of the annulus and, in some cases, the nucleus as well. Such reconstruction prevents recurrent herniation following a microlumbar discectomy. The invention may also be used in the treatment of herniated discs, annular tears of the disc, or disc degeneration, while enabling surgeons to preserve the contained nucleus. The method and apparatus of the present invention may be used to treat discs throughout the spine, including the cervical, thoracic, and lumbar spines of humans and animals.

The present invention also enables surgeons to reconstruct the annulus and, if desired, to replace or augment the nucleus. Novel nucleus replacements may be added to the interior of the disc. Annulus reconstruction prevents extrusion of the nucleus replacements through fissures in the annulus. The annulus reconstruction prevents disc herniation that may cause back and leg or arm pain. The nucleus replacements may be made of natural or synthetic materials.

Synthetic nucleus replacements may be made of but are not limited to, polymers including polyurethane, silicon, hydrogel, etc., and/or other materials which may include elastomers.

The present invention is related to FIGS. 15A-15F of co-pending U.S. patent application Ser. No. 12/263,753, and FIGS. 5A, 5B, 42F of co-pending U.S. patent application Ser. No. 13/297,789, which patent applications are hereby incorporated herein by reference. Preferred embodiments of the present invention include one or more flexible longitudinal fixation components (e.g., filaments, sutures, etc.) extending across a soft tissue defect, such as a fissure in the annulus. One, two, three, four or more transverse anchor components (e.g., bar anchors), connected to the one or more flexible longitudinal fixation components, are preferably placed behind an inner layer of the annulus on opposite sides of the fissure, so as to anchor the one or more flexible longitudinal fixation components to the annulus, with the one or more flexible longitudinal fixation components extending axially through the annulus and laterally across the fissure so as to hold the fissure closed, whereby to prevent nucleus material from passing out the fissure and pressing on the adjacent nerves, including the spinal cord.

Significantly, it has been discovered that applying significant tension (e.g., about 15N to 25N) to the flexible longitudinal fixation components first in an axial direction substantially perpendicular to the adjacent surface of the annulus, and then in a lateral direction substantially parallel to the adjacent surface of the annulus, provides a significantly improved closure of the fissure in the annulus. More particularly, it has been discovered that applying significant tension (e.g., about 15N to 25N) to the flexible longitudinal fixation components first in an axial direction substantially perpendicular to the adjacent surface of the annulus pulls the transverse anchor components through the nucleus tissue and securely against an inner surface of the annulus, in a sort of "pre-tension" action. Thereafter, applying significant tension (e.g., about 15N to 25N) in a lateral direction substantially parallel to the adjacent surface of the annulus draws the fissure closed in a sort of "closing tension" action.

Significantly, this serial application of a significant axial pre-tension, followed by a significant lateral closing tension, ensures a tight closure of the fissure and hence raises the pressure required to extrude nucleus material through the fissure. Prior to this discovery, flexible longitudinal fixation components were secured at a maximum of about 6N tension, and even then in only a lateral direction substantially adjacent to the posterior surface of the annulus, which failed to pull anchor components through the nucleus tissue and against the inner layer of the annulus tissue. Such failure resulted in a relatively loose closure of the fissure, which enabled nucleus material to extrude through the fissure.

It has further been discovered that, by increasing the tensile force applied to the flexible longitudinal fixation components to about 15N to 25N, and by sequentially applying the tensile force first in an axial direction substantially perpendicular to the adjacent surface of the annulus (i.e., in a pre-tension action) and thereafter in a lateral direction substantially adjacent to the posterior surface of the annulus (i.e., in a closing tension action), the efficacy of the closure is significantly increased, and the force required to extrude nucleus material through the closed fissure is significantly increased.

By way of example but not limitation, it has been found that sequentially applying about 15N to 25N of tensile force to the flexible longitudinal fixation components, first in an axial direction substantially perpendicular to the adjacent surface of the annulus and then in a lateral direction substantially parallel to the adjacent surface of the annulus, increases by 64% the force required to extrude nucleus material through the fissure, as compared to conventional closures effected with flexible longitudinal fixation components using about 6N of tension applied in the single, "parallel-to-the-annulus" direction of the prior art.

For the purposes of clarity of description, the present invention will hereinafter generally be discussed in the context of closing a tear or fissure formed in the posterior annulus of an intervertebral disc, however, it should be appreciated that the present invention is also applicable to closing a tear or fissure formed in another portion of the annulus of an intervertebral disc, or to closing a tear or fissure or other opening formed in another anatomical structure, etc.

FIG. 1 is a schematic view showing apparatus 101 for closing a fissure F in the annulus fibrosus, or "annulus" (A). Apparatus 101 generally comprises cylindrical transverse anchor components (e.g., bar anchors) 102, 104 (FIG. 4) that are slidably mounted on a flexible longitudinal fixation component (e.g., filament, suture, etc.) 110. The flexible longitudinal fixation component 110 passes through one or more holes in each transverse anchor component 102, 104.

The transverse anchor components 102, 104 are preferably about 0.8 to 2 millimeters in diameter, and most preferably about 1.1 to 1.3 millimeters in diameter, and about 3 to 7 millimeters in length, and most preferably about 4 to 5 millimeters in length. The holes in transverse anchor components 102, 104, 106, 108 are preferably about 0.1 to 0.8 millimeters in diameter, and most preferably have a narrow portion of about 0.1 to 0.3 millimeters in diameter and wider portion of about 0.4 to 0.8 millimeters.

The proximal and distal portions of the holes in transverse anchor components 102, 104 are preferably beveled, or have rounded edges, so as to reduce friction between flexible longitudinal fixation component 110 and the transverse anchor components 102, 104, and so as to reduce the risk of the edges of the holes cutting the flexible longitudinal fixation component 110. The transverse anchor components 102, 104 are preferably cylindrical, but may be elongate with a non-circular cross-section in alternative embodiments of the invention. For example, such transverse anchor components 102, 104 may have triangular, square, hexagonal or other shapes in cross-section. Two or more transverse anchor components 102, 104 (e.g., 4 to 8 such transverse anchor components) may be provided for each flexible longitudinal fixation component 110 in alternative embodiments of the invention.

The transverse anchor components 102, 104 may be made of titanium, tantalum, stainless steel, polypropylene, Delrin, polyetheretherketone (PEEK), or any other suitable biocompatible material. By way of example but not limitation, the transverse anchor components 102, 104 may be made of molded PEEK.

The flexible longitudinal fixation component 110 is preferably formed out of suture, e.g., size 2-0 to #4 non-absorbable suture, and most preferably size 2-0 or 1-0 suture. By way of example but not limitation, the flexible longitudinal fixation component 110 may be made of size 2-0 braided suture such as Ethibond (Ethicon, Somerville, N.J.), FiberWire (Arthrex, Naples, Fla.), MaxBraid (Biomet, Warsaw, Ind.), and Orthocord (DePuy, Warsaw, Ind.). The flexible longitudinal fixation component 110 is preferably about 40 to 120 centimeters long, and most preferably about 70 to 95 centimeters long.

The apparatus 101 loaded in the distal end 120 of a needle-like insertion device 122. The longitudinal axes of the transverse anchor components 102, 104, which are co-linear and most preferably co-axial with one another, are loaded in the distal end of the lumen of needle-like insertion device 122. Such needle-like insertion device 122 is described and illustrated in the aforementioned U.S. patent application Ser. No. 12/263,753 and 61/414,186, both of which are incorporated herein by reference. The ends and the central portion of the flexible longitudinal fixation component 110 extend into the lumen of the needle-like device 122 or out through a slot formed in the side of the distal end 120 of the needle-like insertion device 122.

As shown in FIG. 1, the distal end 120 of needle-like insertion device 122 is advanced through the annulus A of the intervertebral disc D on one side of a tear or fissure F and into the nucleus tissue N. A stylet component 127 slidably disposed in the lumen of the needle-like insertion device 122 forces the first transverse anchor components 102 out of the distal end of the needle-like insertion device 122 after the distal end of the needle-like insertion device 122 has passed through the annulus A on a first side of a fissure F in the annulus. The ends and central portion of the flexible longitudinal fixation component 110 are seen extending through the hole in the posterior annulus created by passage of the needle-like insertion device 122.

When the first transverse anchor component 102 is ejected from the distal end of the needle-like insertion device 122 into the nucleus N of the intervertebral disc D, the distal end of the needle-like insertion device 122 must have been advanced a sufficient distance into the nucleus N for the first transverse anchor component 102 to be able to turn (i.e., from the longitudinal orientation of FIG. 1 to the transverse orientation of FIGS. 4, 5 and 6) so as to prevent the first transverse anchor components 102 from being pulled back through the posterior annulus. Note also that at this level of penetration into the nucleus N, a substantial amount of nucleus material will be interposed between the first and transverse anchor component 102 and the inner surface of the posterior annulus.

Figure 2:
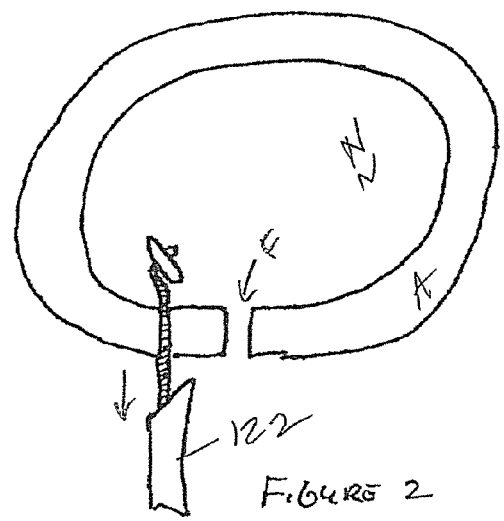
FIG. 2 is a schematic view showing the apparatus of FIG. 1 ejected from the distal end of a needle-like insertion device.

FIG. 2 is a schematic view showing the apparatus 101 in the nucleus tissue and the needle-like insertion device 122 withdrawn from the annulus A on a first side of the fissure F. More particularly, at this point in the procedure, axial tension has been applied to the distal end of the flexible longitudinal fixation component 110 so as to pull the first transverse anchor component through nucleus tissue.

Figure 3:
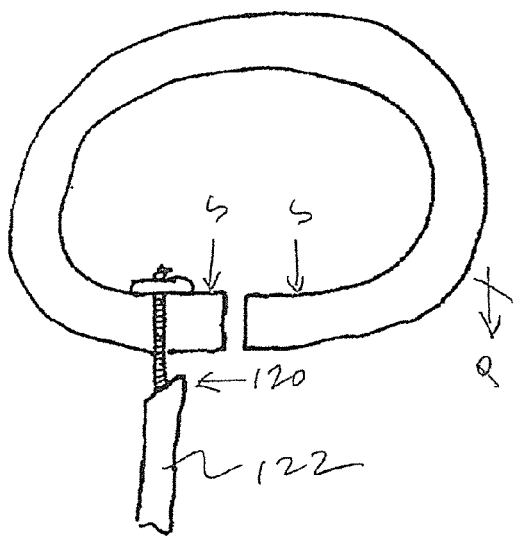
FIG. 3 is a schematic view showing the apparatus of FIG. 2 pulled through nucleus tissue and against the inner layer of the annulus of an intervertebral disc.

FIG. 3 is a schematic view showing the apparatus 101 in the nucleus tissue and the needle-like insertion device withdrawn from the annulus on a first side of the fissure. More particularly, at this point in the procedure, additional axial tension has been applied to the distal end of the flexible longitudinal fixation component 110 so as to pull the first transverse anchor component 102 through nucleus tissue and back against the inner surface S of the posterior annulus. This may be done by pulling on the distal end of flexible longitudinal fixation component 110 in a direction perpendicular to the posterior wall of the annulus with a force of about 15N to 25N so as to pull the first transverse anchor component 102 back through the intervening nucleus material so that the first transverse anchor component 102 seats securely against the inner surface of the posterior annulus. It has been discovered that a force of this direction and magnitude is needed to reliably move the first transverse anchor component 102 through the heavy crabmeat-like consistency of the nucleus N.

Figure 4:
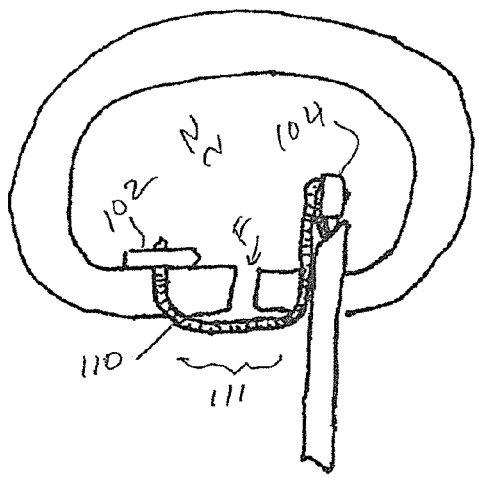
FIG. 4 is a schematic view like that of FIG. 3, but showing the apparatus of FIG. 3 penetrating the annulus on a second side of the fissure.

FIG. 4 is a schematic view showing needle-like insertion device 122 advancing a portion of the apparatus 101 through the annulus A of the intervertebral disc D on a second side of a tear or fissure F and into the nucleus tissue N. The distal 5 to 25 millimeters of the needle-like insertion device 122 may preferably be curved in alternative embodiments of the invention. In addition, the stylet component 127 in the lumen of the needle-like insertion device 122 forces the second transverse anchor component 104 from the distal end of the needle-like insertion device 122 after the distal end of the needle-like insertion device 122 has passed through the posterior annulus on a second side of the fissure F, which is generally opposite to the side on which the previously-inserted transverse anchor component 102 was set. It will be appreciated that as this occurs, a length 111 of the flexible longitudinal fixation component 110 will extend laterally across the fissure F.

Again, when the second transverse anchor components 104 is ejected from the distal end of the needle-like insertion device 122 into the nucleus N, the distal end of the needle-like insertion device 122 must have been advanced a sufficient distance into the nucleus N for the second transverse anchor components 104 to be able to turn (i.e., from the longitudinal orientation of FIG. 4 to the transverse orientation of FIGS. 5 and 6) so as to prevent the second transverse anchor component 104 from being pulled back through the annulus. Note also that at this level of penetration into the nucleus, a substantial amount of nucleus material will be interposed between the second transverse anchor component 104 and the inner surface of the posterior annulus.

Again, axial tension is applied to the flexible longitudinal fixation component 110 to pull the second transverse anchor components 104 through the nucleus tissue and back against the inner surface of the posterior annulus. This may be done by pulling on the distal end of the flexible longitudinal fixation component 110 in a direction perpendicular to the posterior wall of the annulus with a force of about 15N to 25N so as to pull the second transverse anchor component 104 back through the intervening nucleus material so that the second transverse anchor component 104 seats securely against the inner surface of the posterior annulus. It has been discovered that a force of this direction and magnitude is needed to reliably move the second transverse anchor component 104 through the heavy, crabmeat-like consistency of the nucleus N.

Figure 5:
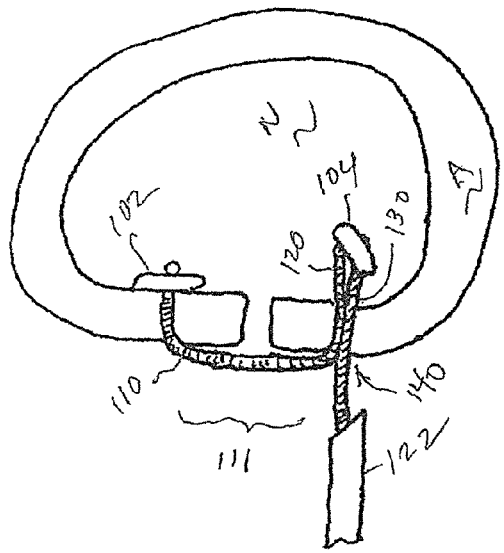
FIG. 5 is a schematic view showing the apparatus of FIG. 4, but showing removal of the needle-like insertion device closing the fissure in the annulus.

FIG. 5 is a schematic view showing the apparatus 101 in the nucleus tissue and the needle-like insertion device 122 withdrawn from the annulus A on a second side of the fissure F. More particularly, at this point in the procedure, axial tension has been applied to the distal end of the flexible longitudinal fixation component 110 so as to pull the second transverse anchor component through the nucleus tissue. A portion 111 of the flexible longitudinal fixation component 110 extends between the first and second transverse anchor components 102 and 104, respectively. The central portion 120 and distal portion 130 of the flexible longitudinal fixation component 110 are seen extending axially through the hole 140 formed in the annulus A by the needle-like insertion device 122.

Figure 6:
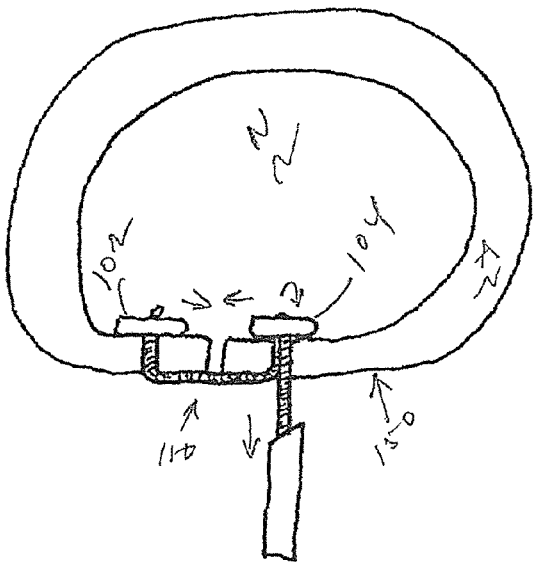
FIG. 6 is a schematic view showing the apparatus of FIG. 6 disposed against the inner surface of the annulus, and fastening of the tensioned flexible longitudinal component two the anchor components at least partially closing the fissure in the annulus.

As shown in FIG. 6, axial tension applied to the distal end of the flexible longitudinal fixation component 110 pulls the second transverse anchor component 104 against the inner surface of the posterior annulus and reduces the length of portion 111 of the flexible longitudinal fixation component 110. Again, this tension should be applied axially (i.e., substantially perpendicular to the posterior wall of the annulus), and at a substantial level (e.g., at about 15N to 25N), in order to ensure proper seating of the transverse anchor component 104 against the inner surface of the posterior annulus.

Once the transverse anchor component 104 has been properly seated against the inner surface of the posterior annulus (i.e., once the transverse anchor components 102 and 104 have been "pre-tensioned"), additional axial tension on the distal end of the flexible longitudinal fixation component pulls distal end of the central portion 120 of the flexible longitudinal through the opening or openings in anchor 104, which applies lateral tension on that portion of the flexible longitudinal fixation component so as to draw the fissure F closed, and then the central portion 120 and distal portion 130 of the flexible longitudinal fixation component 110 may be locked into the opening or openings in anchor 104.

Figure 9:
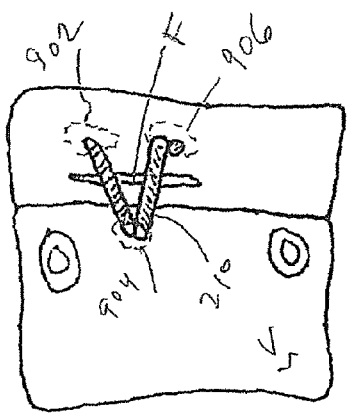
FIG. 9 is a schematic view showing another preferred form of apparatus for closing a fissure in the annulus near a vertebra.
Figure 10:
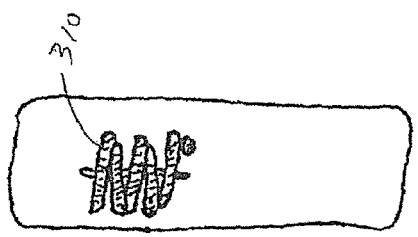
FIG. 10 is a schematic view showing another preferred form of apparatus for closing the fissure in the annulus.

More particularly, FIG. 6 is a schematic view showing how tension (e.g., about 15N to 25N) applied axially to the distal end 134 of the flexible longitudinal fixation component 110 tightens the central portion 111 of the flexible longitudinal fixation component 110, which extends laterally over the fissure or defect F in the annulus. The distal end 134 of the flexible longitudinal fixation component 110 is preferably cut flush with the posterior surface 150 of the annulus in the next step of the procedure. Alternatively, as shown in FIGS. 8, 9, and 10, third, fourth, fifth or more anchors, through which the flexible longitudinal fixation component 110 passes may be passed through the annulus using the same method before the distal end 134 of the flexible longitudinal fixation component 110 is cut and removed.

Thus it will be seen that, with the present invention, a filament (e.g., the flexible longitudinal fixation component 110) is used to laterally span a tear, fissure or other defect in the annulus, with one portion of the filament being anchored to the annulus by passing at least one first anchor (e.g., a transverse anchor component) through the annulus and into the nucleus on one side of the fissure, and with a second portion of the filament being anchored to the annulus by passing at least one second anchor (e.g., a transverse anchor component) through the annulus and into the nucleus on a second side of the fissure, with the at least one first and second anchors being drawn back through the nucleus and against the inner surface of the posterior annulus by the application of a significant (e.g., about 15N to 25N) axial tension applied perpendicular to the posterior wall of the annulus (i.e., by a "pre-tension"), and with the fissure being drawn closed by the subsequent application of a significant (e.g., about 15N to 25N) axial tension applied perpendicular to the posterior wall of the annulus (i.e., by a "closing tension"), and with portions of the filaments thereafter being secured to one or more anchors (e.g., by press fit into slots in the second anchor) so as to hold the fissure closed.

Figure 7:
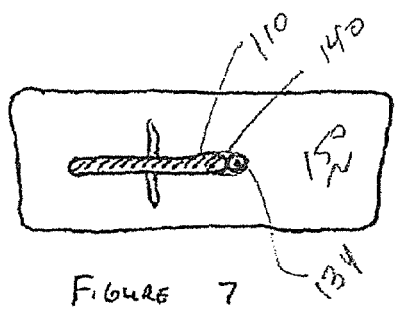
FIG. 7 is a schematic view showing the apparatus of FIG. 1 disposed against the outer surface of the annulus.

FIG. 7 is a schematic view showing the surface 150 of the posterior annulus and the flexible longitudinal fixation component 110 in position. The distal end 134 of the flexible longitudinal fixation component 110 is seen extending through hole 140 in the annulus. High tension on the flexible longitudinal fixation component 110 creates a stiff construct spanning the fissure F, which resists pressure from the nucleus N trying to extrude through the closed fissure F.

Figure 8:
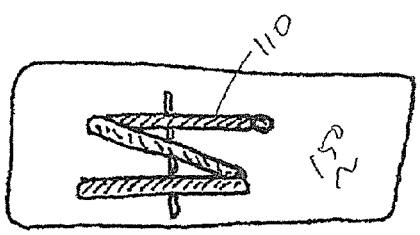
FIG. 8 is a schematic view showing another preferred form of apparatus for closing a fissure in the annulus.

FIG. 8 is a schematic view showing the surface 150 of the posterior annulus and the flexible longitudinal fixation component 110 in an alternative embodiment of the invention shown in FIG. 7. Flexible longitudinal fixation component 110 extends from a first anchor placed in the caudal portion of the annulus on the left side of the fissure to a second anchor placed in the caudal portion of the annulus on the right side of the fissure then to a third anchor placed in the cranial portion of the annulus on the left side of the fissure then to a fourth anchor placed in the cranial portion of the annulus on the right side of the fissure.

The second, third, and fourth anchors have features that permit sliding of portions of flexible longitudinal fixation component 110 through those anchors then fastening or locking of portions of flexible longitudinal fixation component 110 to those anchors. Axial tension of about 15N to 25N or more is preferably applied to the distal end of flexible longitudinal fixation component 110 following insertion of each such anchor so as to pull each anchor through the nucleus and against the inner layer of the annulus and to reduce the length of the central portions of flexible longitudinal fixation component 110, which narrows the fissure in the annulus. Locking portions of flexible longitudinal fixation component 110 in two or more anchors maintains tension on most of the flexible longitudinal fixation component 110 should locking mechanisms in one or two anchors fail.

FIG. 9 is a schematic view showing an alternative embodiment of the present invention. More particularly, FIG. 9 shows flexible longitudinal fixation component 210 passing from a first anchor 902 placed behind the annulus cranial on the left side and above transverse fissure F to a second anchor 904 placed in the cranial portion of a vertebra V, then to a third anchor 906 placed behind the annulus cranial to a transverse fissure on the right side of that fissure. The first and third anchors have the locking feature.

In FIG. 10, the flexible longitudinal fixation component 310 passes from a first anchor placed behind the annulus caudal to a transverse fissure on the left side of that fissure to a second anchor placed in behind the annulus cranial to the transverse fissure on the left side of that fissure followed by third, fourth, fifth, and sixth anchor placed sequentially caudal then cranial to the fissure in the annulus. The second through sixth anchors have the locking feature. Five, seven, eight, or more anchors connected by a single flexible longitudinal fixation component can be used in alternative embodiments of the invention. Alternatively, two or more flexible longitudinal fixation components connecting at least two anchors each could be used in alternative embodiments of the invention. As with other embodiments described herein, considerable axial tension is applied to the flexible longitudinal fixation component 310 to seat each anchor prior to deployment of the next.

Anchors that permit sliding of portions of one or more flexible longitudinal fixation components through such anchors then locking or fastening of portions of such one or more flexible longitudinal fixation components are used in preferred embodiments of the invention. Preferred anchors could have cleat mechanisms or alternative locking mechanisms. For example, elastic projections from the sides of openings in the anchors could permit sliding of flexible longitudinal fixation components in a first or tightening direction, but prevent sliding of those flexible longitudinal fixation components from sliding in the opposite direction.

Anchors made of shape memory materials such as Nitinol may be used in certain embodiments of the invention. Alternatively, removable elongate components could hold elastic projections from the sides of openings in anchors in an "open" position, which permits sliding of flexible longitudinal fixation components through the anchors. Removal of such elongate projections after tightening the flexible longitudinal fixation components allows the elastic projections to move thereby trapping the flexible longitudinal fixation component between the elastic projections and other portions of the anchor, which fastens or locks the flexible longitudinal fixation component to the anchor.

Figure 11:
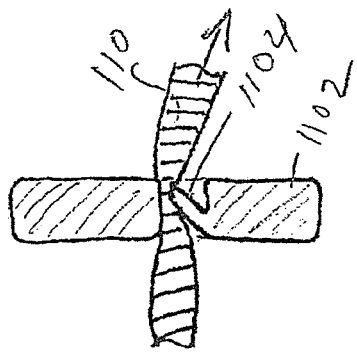
FIG. 11 is a schematic view showing another preferred form of apparatus for closing the fissure in the annulus.

FIG. 11 is superior view of a partial longitudinal cross section a preferred form of apparatus for closing the fissure in the annulus. A portion of the flexible longitudinal fixation component 110 is seen passing through a hole in transverse anchor component 1102. A projection 1104 from one side of the transverse anchor component permits the flexible longitudinal fixation component to easily slide through the anchor component in a first direction indicated by the arrow, but resist sliding of the flexible longitudinal fixation component in a second direction.

Figure 12:
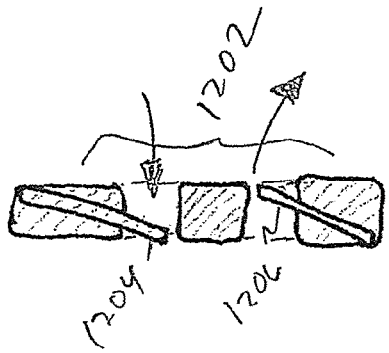
FIG. 12 is a schematic view showing another preferred form of apparatus for closing the fissure in the annulus.

FIG. 12 is a superior view of a flexible longitudinal fixation component (not shown) passes through two openings in transverse anchor component 1202. Projections 1204, 1206 into the openings in the transverse anchor component permit the flexible longitudinal fixation component to easily slide through the anchor in the directions shown, but resist sliding of the flexible longitudinal fixation component in the opposite direction. The projection components 1204, 1206 could preferably be made of first material, such as titanium while the transverse anchor component is made of a second material, such as PEEK. The anchor component of FIG. 12 may be used for either of the anchors 102, 104 shown in FIG. 6, for example.

Figure 13:
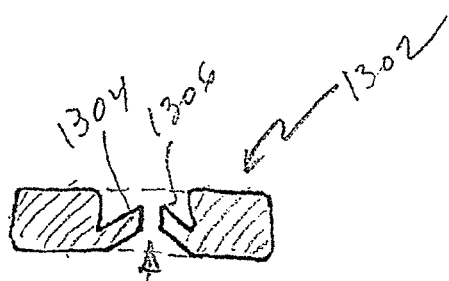
FIG. 13 is a schematic view showing another preferred form of apparatus for closing the fissure in the annulus.

FIG. 13 is a superior view of a longitudinal cross section of anchor 1302. Projections 1304, 1306 are seen extending from two portions of transverse anchor component 1302. The projections permit the flexible longitudinal fixation component to easily slide through the anchor component in a first direction depicted with the arrow, but resist sliding of the flexible longitudinal fixation component in a second direction.

Figure 14:
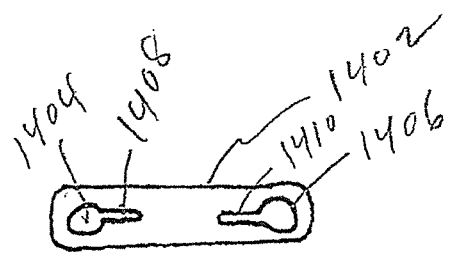
FIG. 14 is a schematic view showing another preferred form of apparatus for closing the fissure in the annulus.
Figure 15:
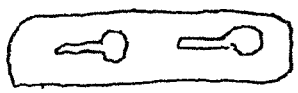
FIG. 15 is a schematic view showing another preferred form of apparatus for closing the fissure in the annulus.
Figure 16:
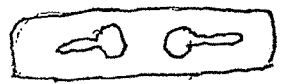
FIG. 16 is a schematic view showing another preferred form of apparatus for closing the fissure in the annulus.
Figure 17:
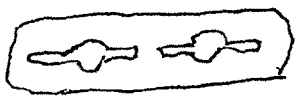
FIG. 17 is a schematic view showing another preferred form of apparatus for closing the fissure in the annulus.

FIG. 14 is a superior view of a further alternative anchor component 1402. Two holes 1404, 1406, are shown passing through transverse anchor component 1402. The generally circular lateral portions of the holes are larger than the narrow slit-like medial portions 1408, 1410 of those holes. The transverse anchor components 102 is preferably about 0.8 to 2 millimeters in diameter, and most preferably about 1.1 to 1.3 millimeters in diameter, and about 3 to 7 millimeters in length, and most preferably about 4 to 5 millimeters in length. The holes in transverse anchor component 102 are preferably about 0.1 to 0.8 millimeters in diameter, and most preferably have a narrow portion of about 0.1 to 0.3 millimeters in diameter and wider portion of about 0.4 to 0.8 millimeters. The flexible longitudinal fixation component (not shown) slides easily through the transverse anchor component when flexible longitudinal fixation component resides in the larger circular-like portions of the holes. The flexible longitudinal fixation component is forced into the narrow slit-like openings of the transverse anchor component to prevent or restrict such sliding after tensioning the flexible longitudinal fixation component. FIGS. 15-17 illustrate alternate slit configurations.

It should be understood that many additional changes in the details, materials, steps and arrangements of parts, which have been herein described and illustrated in order to explain the nature of the present invention, may be made by those skilled in the art while still remaining within the principles and scope of the invention.

The invention claimed is:

1. A method of closing a fissure or other defect in an annulus fibrosus (AF) having an outer surface and an inner surface, the method comprising the steps of:
    providing a flexible longitudinal fixation component terminating in a distal end coupled to a first anchor component, and a proximal second anchor component slidingly coupled along the flexible longitudinal fixation component, wherein at least one of the first anchor component and the second anchor component comprise a hole for receiving the flexible longitudinal fixation component and a projection for (i) permitting the flexible longitudinal fixation component to slide through the hole in a first direction, and (ii) preventing the flexible longitudinal fixation component from sliding through the hole in a second direction;
    inserting the first anchor component through a first insertion point in the AF from the inside out on one side of the defect in the AF such that the first anchor component passes the inner surface of the AF and a first exposed portion of the flexible longitudinal fixation component extends outwardly from the first insertion point;
    applying tension to the first exposed portion of the flexible longitudinal fixation component such that the first anchor component becomes firmly seated against the inner surface of the AF;
    inserting the second anchor component through a second insertion point in the AF from the inside out on the other side of the defect in the AF such that the first exposed portion crosses over the defect and into the second insertion point, and a second exposed portion of the flexible longitudinal fixation component extends outwardly from the second insertion point; and
    applying tension to the second exposed portion such that the flexible longitudinal fixation component slides through the second anchor component, applying tension to the first exposed portion, thereby closing the defect in the AF and causing the second anchor to become firmly seated against the inner surface of the AF.

2. The method of claim 1, wherein the tension applied to the first exposed portion is in the range of about 15 N to 25 N.

3. The method of claim 1, wherein the tension applied to the second exposed portion is in the range of about 15 N to 25 N.

4. The method of claim 1, wherein the flexible longitudinal fixation component is a surgical suture.

5. The method of claim 1, wherein the projection prevents further sliding of the flexible longitudinal fixation component following the step of applying tension to the second exposed portion.

6. The method of claim 1, wherein the process is repeated with one or more additional anchors slidingly coupled at different points along the flexible longitudinal fixation component such that two or more exposed portions cross of the defect when the process is completed.

7. The method of claim 1, wherein the one or both of the anchor components are elongated such that they penetrate the AF axially and turn once past the inner surface of the AF to better prevent pull-out.

8. The method of claim 1, wherein the one or both of the anchor components are inserted with a pointed, cannulated insertion instrument that penetrates the AF and deploys each anchor component with a stylus or push rod.

9. The method of claim 1, including the step of anchoring the flexible longitudinal fixation component to one of an upper and lower vertebral body.

10. The method of claim 1, including the step of trimming the second exposed portion of the flexible longitudinal fixation component.

11. The method of claim 1 wherein the hole is substantially perpendicular to the longitudinal axis of the anchor component.

12. The method of claim 1 wherein the anchor component comprises two holes, and further wherein the two holes are substantially perpendicular to the longitudinal axis of the anchor component.

\* \* \* \* \*